US012712054B2

(12) United States Patent
Dong et al.

(10) Patent No.: US 12,712,054 B2
(45) Date of Patent: Aug. 18, 2026

(54) DIABETES ONSET AND PROGRESSION PREDICTION USING A COMPUTERIZED MODEL

(71) Applicant: Humana Inc., Louisville, KY (US)

(72) Inventors: Yanting Dong, Lexington, KY (US); Jing Fan, Louisville, KY (US); Vinay Chiguluri, Louisville, KY (US); Vipin Gopal, Louisville, KY (US)

(73) Assignee: Humana Inc., Louisville, KY (US)

( * ) Notice: Subject to any disclaimer, the term of this patent is extended or adjusted under 35 U.S.C. 154(b) by 539 days.

(21) Appl. No.: 17/962,732

(22) Filed: Oct. 10, 2022

(65) Prior Publication Data

US 2023/0035564 A1 Feb. 2, 2023

Related U.S. Application Data

(63) Continuation of application No. 14/942,592, filed on Nov. 16, 2015, now abandoned.

(60) Provisional application No. 62/079,962, filed on Nov. 14, 2014.

(51) Int. Cl.

| | |
|---|---|
| ***G16H 10/20*** | (2018.01) |
| ***G16H 10/40*** | (2018.01) |
| ***G16H 50/20*** | (2018.01) |
| ***G16H 50/30*** | (2018.01) |
| ***G16H 50/50*** | (2018.01) |

(52) U.S. Cl.

CPC ............ *G16H 10/20* (2018.01); *G16H 10/40* (2018.01); *G16H 50/20* (2018.01); *G16H 50/30* (2018.01); *G16H 50/50* (2018.01)

(58) Field of Classification Search

CPC ........ G16H 10/20; G16H 50/50; G16H 10/40; G16H 50/30; G16H 50/20

See application file for complete search history.

(56) References Cited

U.S. PATENT DOCUMENTS

2014/0095186 A1* 4/2014 Gotz ................. G06Q 10/0637 705/2

OTHER PUBLICATIONS

Verduijn, M. et al., Temporal Abstraction for Feature Extraction: A Comparative Case Study in Prediction From Intensive Care Monitoring Data, Artificial Intelligence in Medicine, 2007, pp. 1-12, vol. 41.

* cited by examiner

*Primary Examiner* — Jerry Lin

(74) *Attorney, Agent, or Firm* — Standley Law Group LLP; Jeffrey S. Standley; Adam J. Smith

(57) ABSTRACT

The disclosed computerized system and method facilitates predicting the onset of diabetes or symptom progression in those patients already suffering from the disease. The computerized system and method applies steps to segment the population by predefined member characteristics. Once segmented, the computerized system and method applies a plurality of prediction models to the segmented population data to provide a ranking of members of the population that indicates the likelihood of onset or progression of diabetes for each member.

14 Claims, 7 Drawing Sheets

| | Top Predictors |
|---|---|
| **Clinical** | Claim counts |
| | Drug class counts |
| | Physician visit counts |
| | Test cost |
| **Risk** | Obesity |
| | Smoking |
| | MA risk score |
| | RX risk score |
| | Global risk |
| **Demographics** | Race |
| | Education level |
| | Active month |

*FIG. 4*

| | DCSI Model | | | Binary DCSI Grouping Model | | |
|---|---|---|---|---|---|---|
| | Simulated ROC | Top 10% Capture Rate | Top 30% Capture Rate | ROC | Top 10% Capture Rate | Top 30% Capture Rate |
| Low/Medium → High | 0.902 | 66% | 91% | 0.908 | 66% | 92% |
| Low → Medium/High | 0.790 | 30% | 65% | 0.796 | 30% | 66% |
| ΔDCSI ≥ 2 | 0.685 | 23% | 50% | 0.687 | 23% | 51% |

DIABETES ONSET AND PROGRESSION PREDICTION USING A COMPUTERIZED MODEL

CROSS-REFERENCE TO RELATED APPLICATIONS

This application is a continuation of U.S. application Ser. No. 14/942,592, filed Nov. 16, 2015, which claims priority to U.S. Provisional Patent Application Ser. No. 62/079,962, filed Nov. 14, 2014, the contents of each of which are incorporated herein by reference.

BACKGROUND AND SUMMARY OF THE INVENTION

The world health organization estimates that the incidence of diabetes in the United States will almost double during the time period of 2000-2030. The Centers for Disease Control and Prevention estimated that in 2010 there were 26 million people in the United States that had diabetes, with greater than 25 percent of that number being undiagnosed. The National Diabetes Information Clearinghouse has estimated that diabetes costs in the United States are $132 billion a year.

As noted above, it has been estimated that greater than 25 percent of those with diabetes in the United States are unaware of their condition. Patients who are unaware of their diabetes are at greater risk for a worsening of the disease or other health conditions and complications that arise as the result of the failure to treat their undetected diabetes. As with many other types of diseases, the symptoms of diabetes may vary along a continuum from minor to severe. In addition to greater health risks as the result of failure to treat their diabetic condition, a worsening of a patient's condition may markedly increase their cost of care. Treatment cost data indicates that a patient with high severity diabetes may have costs that are eight times as much as a patient with low severity symptoms. There are three types of diabetes: type I; type II; and gestational diabetes. As its name suggests, gestational diabetes is a complication of pregnancy and not suffered by the population at large. Type I diabetes is genetic in origin, non-preventable, but fortunately accounts for only 5% of diabetes. The more prevalent type of diabetes is type II. Type II diabetes is preventable or at least controllable through the implementation of a healthy lifestyle and medication. Therefore, approximately 95% of diabetes instances may be prevented or controlled by lifestyle changes and medication. Additionally, without treatment, diabetes can progress in severity to the point that a buildup of glucose in the patient's bloodstream may result in such complications as cardiovascular disease, vision loss, kidney failure, and even amputation of limbs. However, to treat or prevent progression of the disease, a patient must be aware of his or her diabetic condition. Therefore, prediction may be extremely beneficial to help care providers identify those persons who may have a high risk of developing diabetes. Further, identification of those who currently have diabetes who may be at risk of worsening symptoms is key to help those patients suffering from diabetes effectively manage their condition to avoid or minimize disease progression and the resulting negative health impacts.

Caregivers and insurance providers also may have an interest in detecting a patient's diabetic or pre-diabetic condition. In addition to detection, caregivers and insurance providers may have an interest in predicting the likelihood that a patient currently exhibiting symptoms of the disease will progress to worsening levels of diabetes symptoms. As noted above, the cost to treat a patient's diabetic condition increases dramatically as that patient progresses from less severe to more severe diabetes symptoms. Therefore, a prediction of the likelihood that a segment of population may be at greater risk of developing or suffering a progression of an existing disease condition may be used by caregivers and insurance providers to identify patients with higher levels of risk and proactively initiate monitoring and the provision of appropriate care.

More aggressive monitoring may help to detect the onset of diabetes while increased levels of care may prevent that onset. For persons who already have diabetes symptoms, increased levels of care may prevent the disease from progressing to more severe stages. In either case, in addition to helping persons avoid diabetes entirely or minimize the progression of symptoms, monitoring that results in earlier detection or proactive care may have the additional benefit of reducing the cost of providing care or health insurance to such a person.

What is needed is a computerized system and method for identifying segments of a non-diabetic population that are most likely to develop diabetes over an identified period of time. Also needed is a computerized system and method for identifying those segments of a diabetic population that are likely to experience a progression in the severity of their diabetes and related complications.

Such a system and method may use a severity index to both identify the severity of a diabetic condition and predict the likelihood of disease progression. In embodiments of the invention, input data for use by a predictive model may be collected from a population group. An example of such a group may be persons who are provided coverage by a health insurance provider. In an embodiment of the invention, input data may comprise insurance claims, lab test results, participation in health improvement programs, the output of medical and insurance claim data analysis systems, Medicare data, survey data, population demographics and other population characterizing data. This data may be processed to optimize and transform the various data components into analyzable population data. After optimization, data may be further processed to segment the data into population segments with common data characteristics and detail levels. Predictive models may then be applied to each segment to predict diabetes occurrence and progression risk for population members who are suffering from diabetes at the time of analysis. Once such predications have been performed, actions such as testing, treatment, or counseling may be implemented to reduce the predicted occurrences and slow the progression of the disease in those population members which exhibit symptoms.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIG. 4 is a chart of the member data characteristics that were top predictors of the incidence of diabetes in those members who were not diabetic at the time the analysis was performed;

DETAILED DESCRIPTION OF EXEMPLARY EMBODIMENT(S)

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

In an example embodiment, a model to predict the likelihood of the onset of diabetes is integrated into a software application that may be used by a health insurance provider to predict such a likelihood within a covered patient-member population. As described herein, a model to predict the onset of diabetes may retrieve and analyze data from a population that may be susceptible to the development of diabetes. There are many sources of population health data; however, in an embodiment for use by health insurance providers, one source of such data particular to health insurance providers may be claims and health records for the patient-members who form the population. As noted above, an insurance company may have a particular interest in the subject of this invention to assist in the provision of care to individuals who are members of a health plan. In addition to providing improved levels of care to such individuals, early detection and management may reduce the cost of care and thus the cost of health coverage for the member, improving the financial performance of an insurance provider. While the invention should not be interpreted as being limited to health plan members, the term "members" will be used to describe a population for which data is analyzed to predict the onset or progression of diabetes in embodiments of the invention. In other embodiments, those individuals whose medical information and characteristics are being analyzed may be patients of a care provider and thus may be referred to as patients. Other embodiments of the invention may be used to predict the progression of an existing diabetic disease. Such embodiments may utilize data similar to embodiments which predict the onset of diabetes. These embodiments may also be integrated into a software application used to analyze the input data and generate such predictions. As noted above, such embodiments may be useful for health plan providers, healthcare providers, and other organizations concerned with the health of population members, and as such, interpretation of this description should not be limited to applications utilized by health plan providers only.

Figure 1:
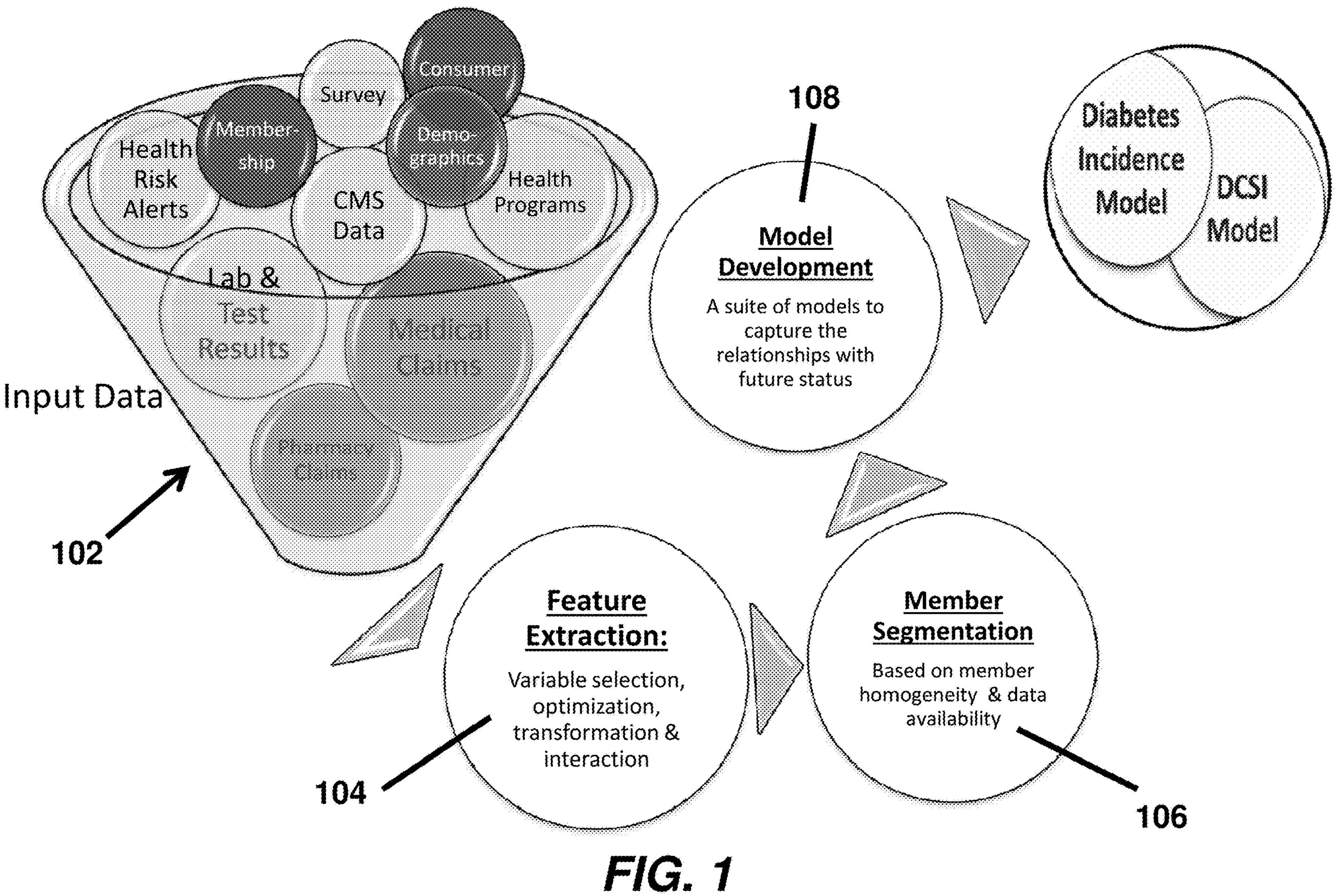
FIG. 1 is an illustration of modeling process in which data is input and used to develop predictive models.

Referring to FIG. 1, input data 102 may be comprised from a plurality of sources. These sources may include both data source from public repositories such as Medicaid/Medicare data (CMS Data) and information derived from consumers of medical services. Other sources of data may be derived from member data maintained by health plan providers. Examples of such information may be member health surveys, membership demographics, membership in certain healthcare groups, and participation in various health programs, summarized lab test results, claims for medical care, claims for pharmacy services, and consumer data. One example of health surveys which may be used in embodiments of the invention is the Medicare Domain Assessment Tool, in which questions about the patient's health/frailty/mental status are asked. For the membership information, the past coverage of the members may be obtained, which may allow an embodiment of the invention to normalize the past healthcare resources utilizations. A health care provider may provide various disease management programs to help members manage their clinical conditions. The participation of the programs may also provide valuable information about patient's health status and future behavior. Consumer data may provide information about the socio-economic status of a member, such as estimated household income, education, and life-style, which may also play a significant role in predicting the disease progression. Another source of data may be comprised of calculated member data such as health risks alerts generated by a medical analytics system. Input data may also include data from medical records, data from health monitoring devices, social media data, and other sources of data which provide patent behavior or characteristics information.

Because of the diversity of sources from which input data 102 may be comprised, a data feature extraction process 104 may be implemented to identify data variables from the various sources. Extracted data may be optimized through the use of summarization, standardization, and filtration processes. The extracted features may describe the patient's demographic profile, clinical profile, behavior profile, medication profile, and disease progression profiles. Example member demographic profile features may include age, gender, race, and socio-economic status; example, clinical profiles include chronic conditions, mental health conditions, hospitalizations, medication etc.; example behavior profiles include health program participations; example medication profile includes adherence to various medications, such as diabetes, heart failure, coronary artery disease, etc.; example progression profiles include characteristics that describe the disease progression history. In addition to standardization and filtration, data may be analyzed to detect interactions between the various data sources. An example of such analysis may be processing Medicaid and Medicare record information to identify population risks related to a particular characteristic of a segment of the public. That characteristic may then be used to identify segments of the member data from a health plan provider to optimize the presentation of member data with regard to the identified characteristic.

When data has been processed to extract and transform key data features into standardized data formats, the members identified by the extracted and transformed data may be segmented based on characteristic homogeneity and data availability 106. Such segmentation may be performed based on information comprised from within the member data. Segmentation may also be performed based on a variety of hypotheses that are applied to member data. Example hypotheses may include, but are not limited to, new members, continuous or existing members, line of business, and other such factors that differentiate members of the population. These examples may be used alone or in combination. Once segmented, the data may have a plurality of models applied to capture the relationship between a member's data characteristics and potential future health conditions for that member 108.

The results of this plurality of models as well as the methods used to segment the population may be subject to various forms of validation testing. Examples of such testing may be the application of models to validate data in order to identify models exhibiting the desired level of performance and then an application of the model to a larger and independent set of test data to verify the results match those of the smaller validation population. This testing may serve to identify the most accurate methods of segmentation and applied models with regard to the predictions derived from their application to sample population data. Once these models are identified, they may be applied to new data in order to perform the prediction and identification desired by the health care or health plan provider which is responsible for the member or patient population.

In another embodiment of the invention, data models may be used to predict the progression between various stages of diabetes for those members who have already begun to exhibit disease symptoms. As with the previously described embodiment, input data 102 may be comprised from a plurality of different sources. These sources may include both data source from public repositories and from non-public sources such as such as member data maintained by a health plan provider. Another source of data may be comprised of calculated data as was described above.

Figure 2:
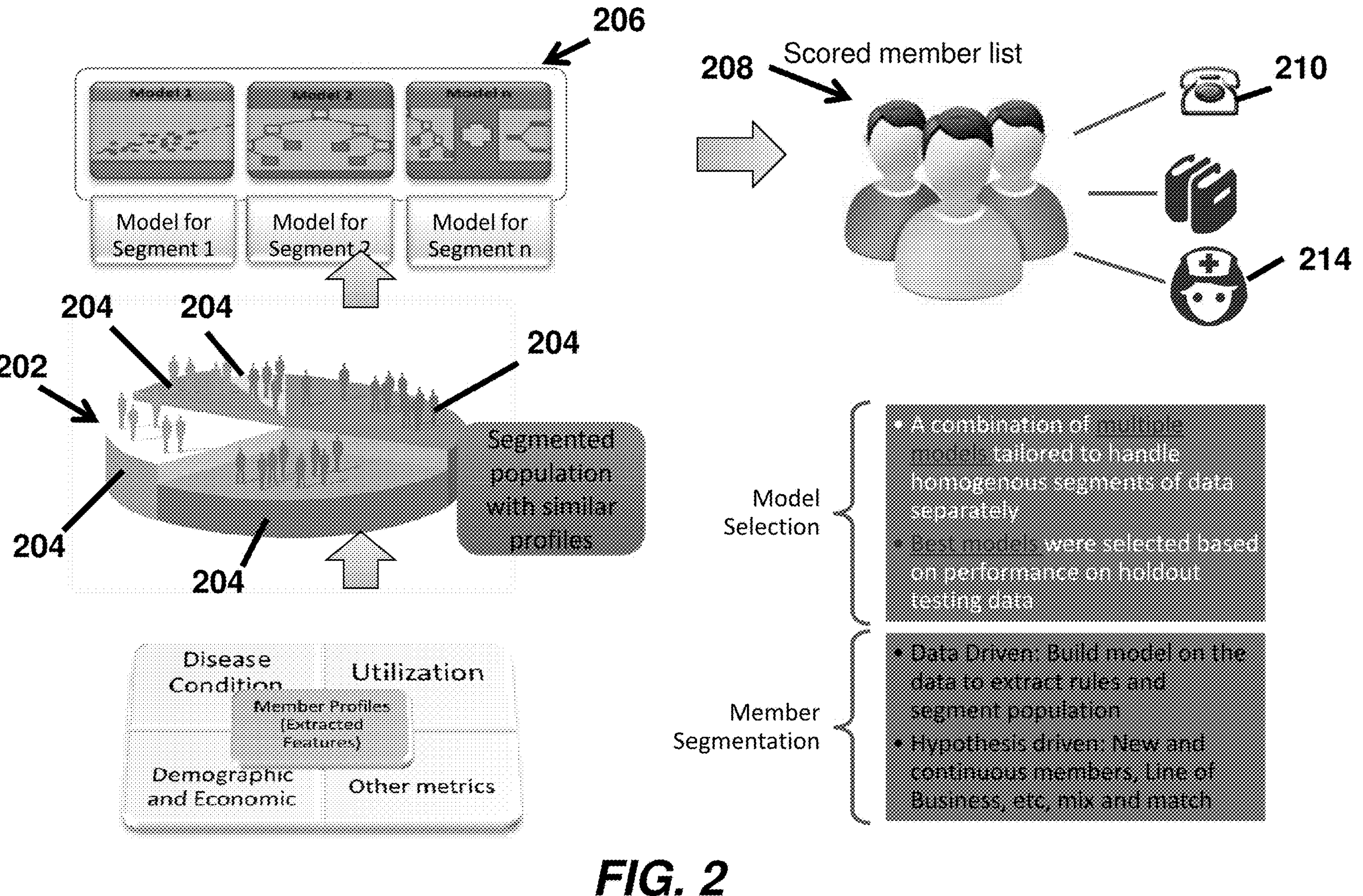
FIG. 2 is a graphic illustration of a system for analyzing population data to generate a predicted risk of disease or disease progression when the disease exists in a population member.

FIG. 2 shows an embodiment of the invention that illustrates the use of different models for different population groups identified during a segmentation stage 106. As is illustrated at 202, input data may be gathered and divided into population segments grouped by profile 204. Because these profiles may result in population segments with different risk characteristics, accurate scoring or prediction of member risk may require different models for each population segment. The models may be neural network, logistic regression, decision tree, or similar modeling methods or a combination of several models, i.e., ensemble models. This result is illustrated at 206. To determine the best models for each segment, an embodiment of the invention may apply a plurality of models to each population segment. Holdout test data may be used to verify each model and select that model with the most accurate prediction of disease. Once the best models have been determined for the population segments, an embodiment of the invention may apply those models to segmented population data as illustrated in FIG. 2. Once these models are applied, a list of members 208 may be produced that is scored according to the risk detected by the plurality of models. As is illustrated, the scored member list 208 may be used to initiate phone communications 210 to help the member better manage the condition of a member contained in the list. The list may also be used to contact the member for the provision of information to encourage and assist self-management activities by the member. A scored list may also serve to trigger a visit by a health care provider (here illustrated as a nurse) to a patient 214.

Figure 3:
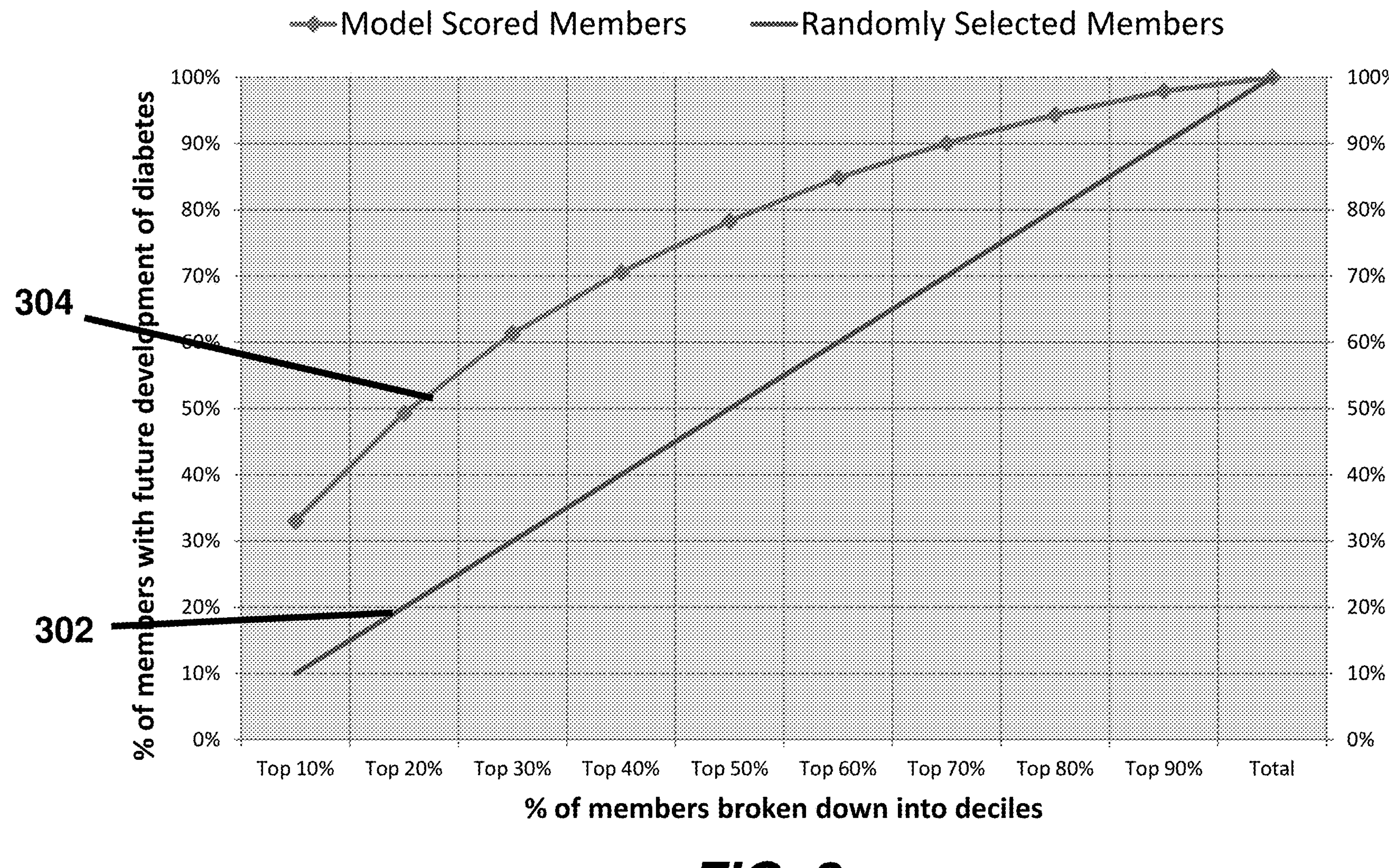
FIG. 3 is an illustration of the output of the modeling process showing a comparison between prediction of the onset of diabetes for members of a population to which risk scores have been assigned and those population members which were randomly selected.

The output of a diabetes incidence prediction model as compared to randomly selected population members is illustrated in FIG. 3. As is shown, the incidence of the development of diabetes in randomly selected members from a health plan is illustrated at 302. In a randomly selected sample, the incidence of diabetes most likely corresponds linearly based on the percentage of members. For example, the top 10% of members corresponds to 10% of the overall development of diabetes, the top 20% of members corresponds to 20% of the overall development of diabetes and so-on as the percentage of members approaches 100%. One skilled in the art will realized that randomly selecting members is not useful for the prediction of the occurrence of diabetes beyond the percentage of the population corresponding to a percentage of the overall number of the population that will develop diabetes. However, the result of the predictive model being applied to the population is illustrated at 304.

As is shown, the scoring applied to the analyzed member data is significantly more likely to predict the occurrence of diabetes in the analyzed population than random selection. For example, in the results of the predictive model, the top 10% of members ranked by the modeled prediction score yielded approximately 33% of those members that developed diabetes. The top 20% of those members ranked according the predictive model yielded approximately 49%, and so-on as the percentage of ranked members is increased. As shown, greater than 60% of those members that will develop diabetes during a predetermined time are identified in the top 30% of the rankings applied to those members analyzed. In other words, the model was twice as likely to identify a member at risk of developing diabetes symptoms as would be selecting members at random. The top predictors used in the model of FIG. 3 are listed in the chart of FIG. 4. For instance, among risk factors identified in the member data, obesity and smoking were top predictors of the development of diabetes.

Figure 5:
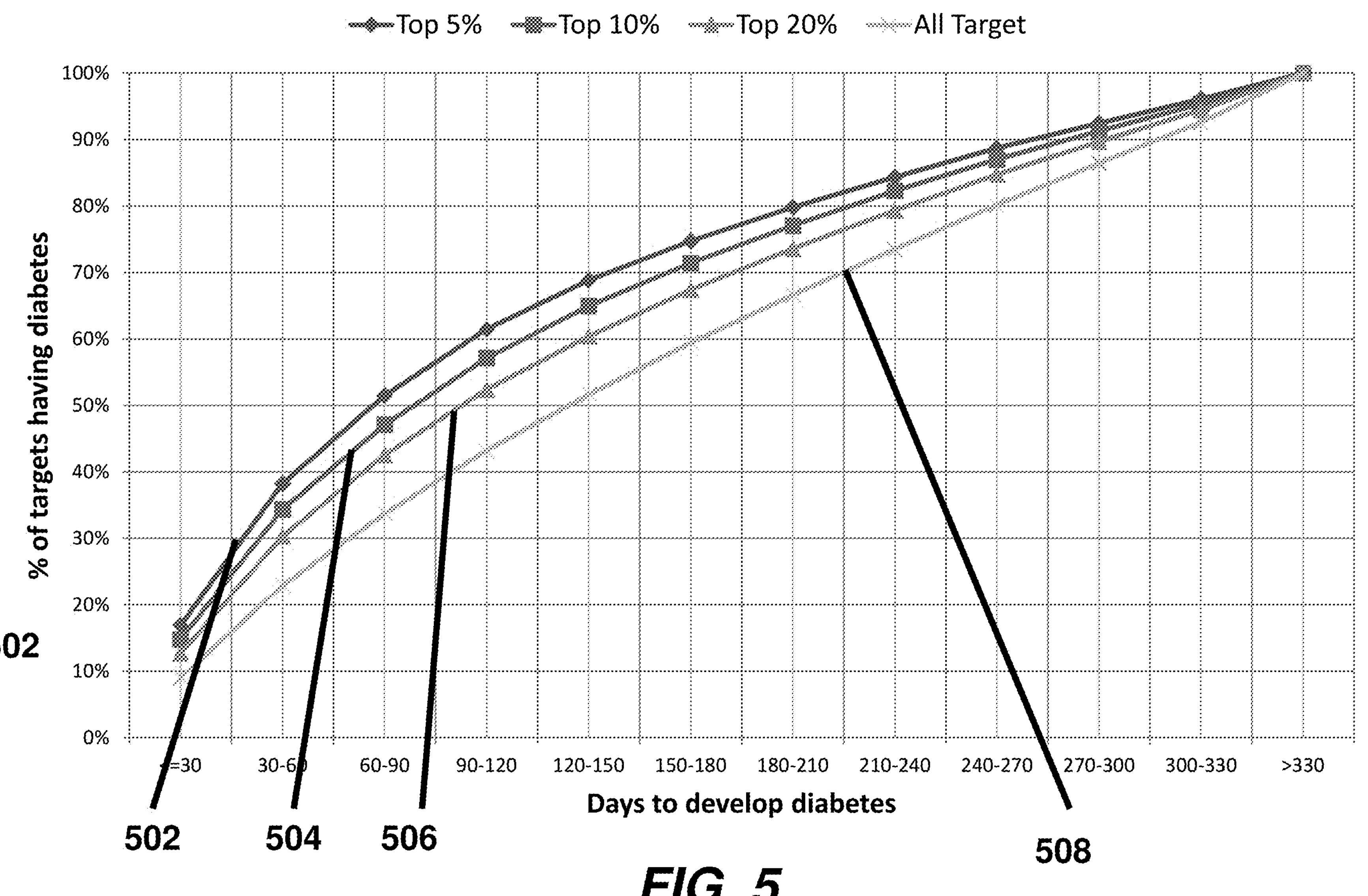
FIG. 5 is a graph showing the percentage of population members with predicted high risk that develop diabetes over a period of time.

In another embodiment of the invention, models may be applied to identify those members at most risk of developing diabetes as time elapses. For instance, referring to FIG. 5, line 502 represents those members ranked in the top 5% by the predictive model. Line 504 represents the top 10%, line 506 represents the top 20%, and line 508 represents the entirety of those members who develop diabetes during the illustrated time period. Moving from left to right along the graph represents the number of days that elapse before an identified member develops diabetes symptoms. Among all member segments, there is a median (50% of members developing diabetes) of at least 60-90 days of time between scoring and developing diabetes, providing time for identified members receiving proactive intervention.

In embodiments of the invention that apply models to predict the progression of a patient's diabetes symptoms, a risk score may be generated that reflects a member's risk of progressing to a higher incidence of diabetes disease complications. Such a risk score may be useful to a health plan or medical care provider seeking to initiate contact with members of the insured population at risk for developing a higher level of disease complications. As noted above, the cost of treating a diabetes patient's disease symptoms increases as the severity of those conditions increases. Thus, identification may allow a care or health plan provider to proactively make contact with a member to encourage that member to take actions to mitigate the risk of such progression. When identifying members at risk of developing increased levels of diabetes symptoms, a system and method may utilize inputs such as Medicaid/Medicare data (CMS Data) and information derived from consumers of medical services. Other sources of data may be derived from member data maintained by health plan providers. Examples of such information may be member health surveys, membership demographics, membership in certain healthcare groups, and participation in various health programs. Another source of data may be comprised of calculated member data such as alerts of identified health risks generated by medical analytics systems, lab test results, claims for medical care, and claims for pharmacy services. The model may also include data from medical record, data from health monitoring devices, social media data, etc.

In embodiments of the invention which predict the progression of a member's diabetes symptoms, the above noted inputs may be combined with a disease severity index used to rate a patient's symptoms relative to a general population. One such severity index is the Diabetes Complications Severity Index (DCSI) which is a standardized methodology used in the healthcare industry to quantify the extent to which body systems in addition to those directly related to the diabetic condition are impacted by the progression of diabetes in a patient. DCSI provides an index score for a patient based upon the presence of cardiovascular, cerebrovascular, metabolic, nephropathy, neuropathy, peripheral vascular disease and retinopathy conditions in the patient. In order to identify the presence of these conditions in a patient, an embodiment of the invention may analyze a patient's medical record data to detect the presence of specific sets of International Classification of Diseases (ICD9) codes. Should codes be detected that indicate one or more of these conditions are present, a point value may be assigned to the identified condition. In an exemplary embodiment employing the DCSI, each condition is assigned a value of one or two points, depending on the condition severity, as described by the ICD9 codes, with the exception of Neuropathy, which is assigned a point value of one. These point values are summed, resulting in a DCSI score ranging from zero to thirteen. A score of zero indicates an absence of any complication condition, and a score of 13 indicates that a patient has indications corresponding to each of the seven identified conditions.

Figure 6:
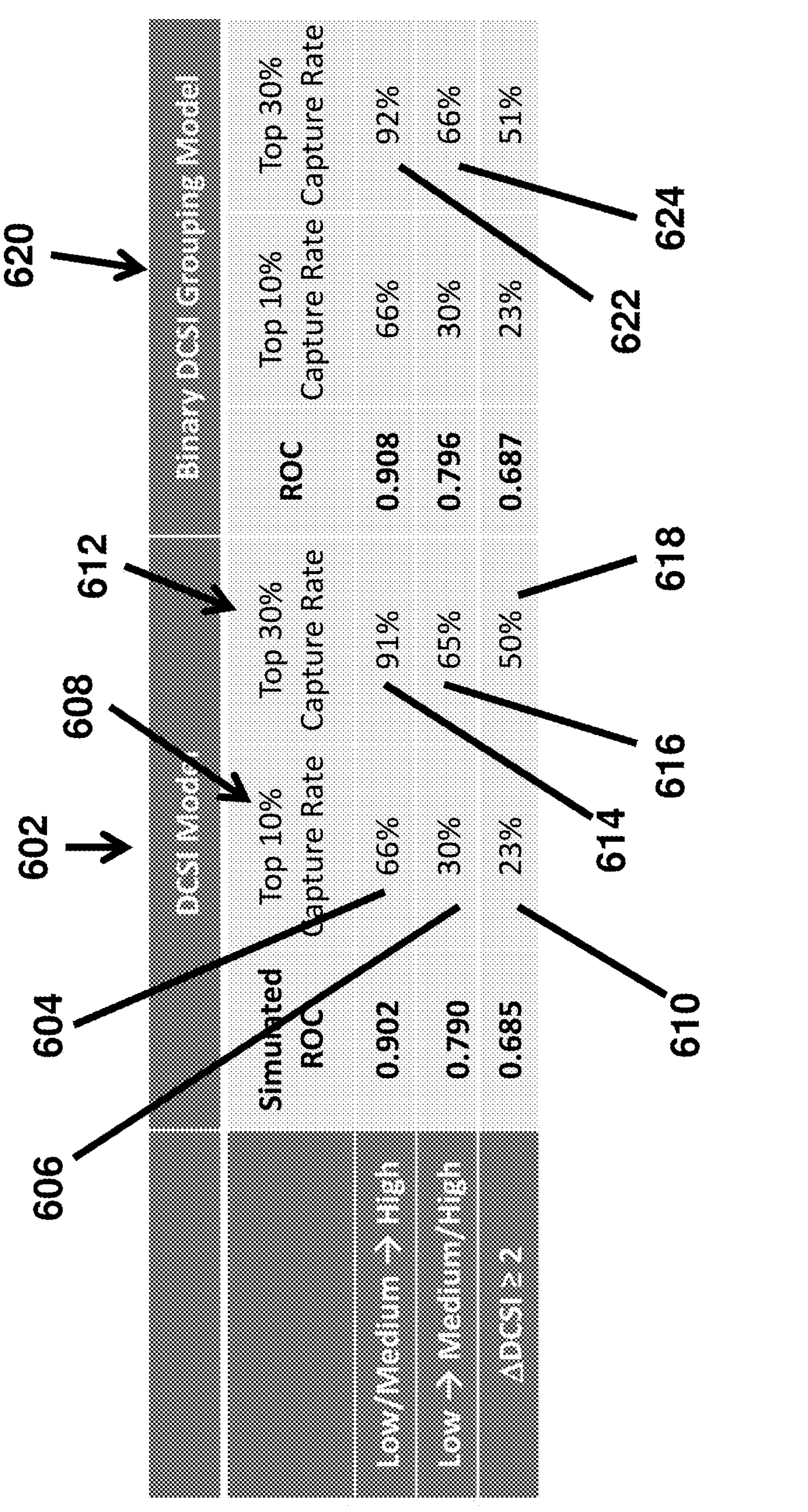
FIG. 6 is a chart of model performance when calculating the predicted progression of diabetes complications among members of a diabetic population.
Figure 7:
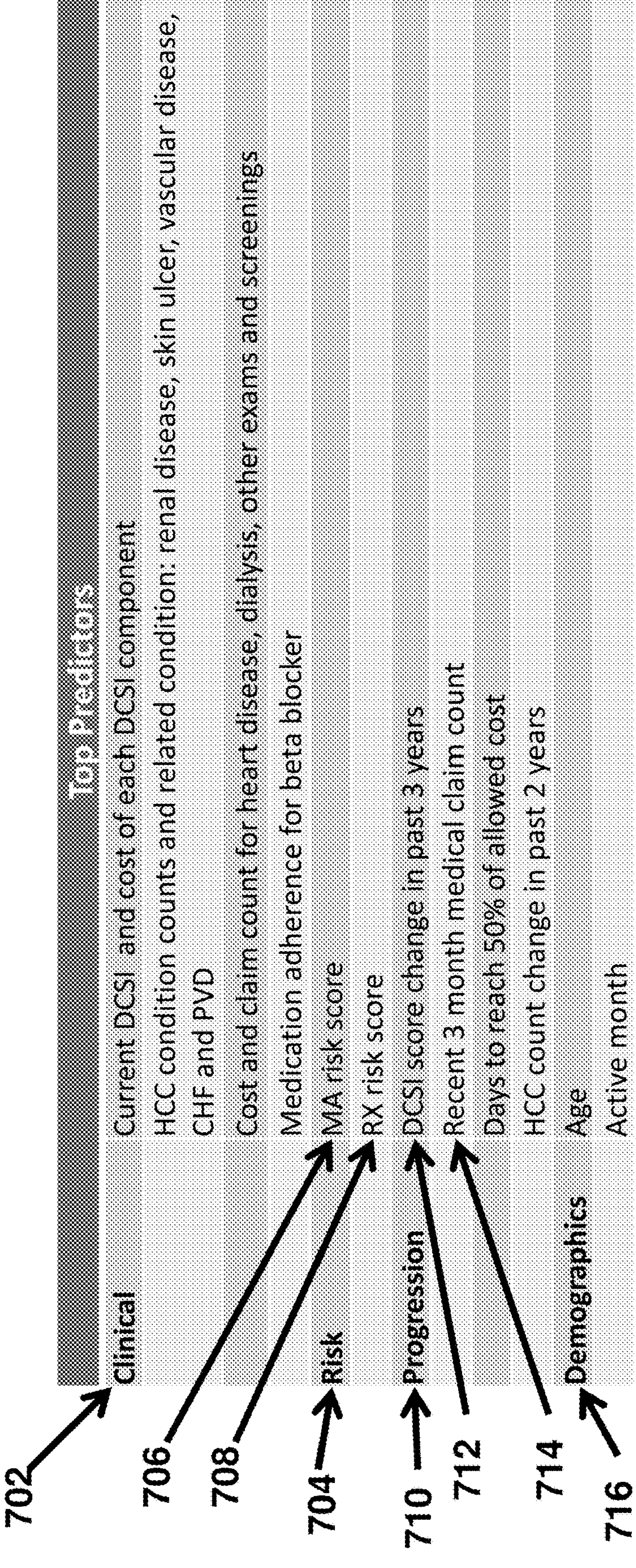
FIG. 7 is a chart of the top predictors of an increase in the progression of diabetes complication among members of a diabetic population group.

FIG. 6 illustrates the performance of two models, based on Medicare patient health data, used to determine the risk of complication progression over a period of time. In order to illustrate the grouping patients using their DCSI scores, three categories were identified, a low severity index range category with DCSI scores ranging from 0-3, a medium severity range with DCSI scores ranging from 4-7, and a high severity category which includes the range of 8-13. In the illustrated figure, a model based on Diabetes Complication Severity Index 602 returns a 66% 604 rate of detections of severity index progression from low/medium to high and 30% 606 from a severity index of low to medium/high for those members in the top 10% of prediction rankings 608. The top 10% also includes 23% of those member's whose DCSI score increases by two or more points 610. Using the same model, those members in the top 30% of prediction rankings 612 comprise 91% of the members whose DCSI score progresses from low/medium to high 614 and 65% of those members whose DCSI score progresses from low to medium/high 616. The top 30% of the prediction rankings also captured 50% of those members whose DCSI score increased by two or more points 618. Receiver operating characteristic (ROC) scores are also shown for each level of progression. These scores indicate the performance of a model taking into account both correct indications as well as those that are incorrectly positive or negative indications. As is illustrated in this example, such a model may permit an entity such as a health plan provider or healthcare provider executing the illustrated model to identify a large percentage of those members or patients at risk of progression to a higher level of diabetes severity. Those members may then be contacted to offer forms of intervention or treatment that may reduce the likelihood of progression. FIG. 6 also illustrates the results of a second model based on binary DCSI groupings 620, in which the prediction target is whether the member has progressed to a more severe stage. As is shown, the top 30% of the prediction rankings produce slightly improved capture rates of those members who progress from low/medium to high DCSI scores 622 and those who progress from low to medium/high DCSI scores 624. In the example models illustrated in FIG. 6, top predictors may be those listed in FIG. 7. As is shown, these predictors may be separated into categories such as clinical predictors 702, risk scores 704 related to Medicare Advantage scores 706 and prescription risk 708. Predictors may also comprise indications of disease progression 710 such as the change in DCSI score over time 712 and the number of medical claims over a period of time 714. In addition to clinical, risk and progression characteristics, the demographic characteristics 716 of a member or patient may also be used to predict the progression of diabetes.

Any embodiment of the present invention may include any of the optional or preferred features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

What is claimed is:

1. A system for improving accuracy in predicting the onset, progression, and severity of diabetes in an insured population using population segment specific modeling based on otherwise disparate, siloed sources, said system comprising:

databases comprising medical data for a plurality of members of an insured population, wherein said medical data is derived from a plurality of otherwise disparate, siloed data sources, including from a plurality of different providers for at least some of the plurality of members, including insurance claims data, lab test result data, clinical data, risk data, data indicating participation in health improvement programs, survey data, and demographic data, wherein at least one of said databases is publicly accessible and at least one of said databases is privately accessible, is associated with a health insurance provider for the insured population, and includes at least some of the insurance claims data;

one or more non-transitory electronic storage devices comprising software instructions, which when executed, configure the one or more processors to:

retrieve said medical data for the members of the population from the databases;

pre-process the retrieved data, including, summarizing, standardizing, and filtering said data received from each of said databases to increase homogeneity of said data;

perform a feature extraction subroutine on said retrieved medical data to extract characteristics for said members of the population;

segment the population into a plurality of segments by at least some of the extracted characteristics, wherein the characteristics comprise (i) date of membership to the population such that segmentation is performed between new members and existing members, (ii) line of business associated with the member such that segmentation is performed between members associated with different lines of business, and (iii) data availability of certain types of said medical data such that segmentation is performed between members associated with different types of data;

for each segment, apply a plurality of different machine learning models to the segment, apply each of the plurality of different machine learning models to a test set of data, determine which of said plurality of different machine learning models provides a highest level of accuracy relative to the test set of data using holdout data, and select the highest accuracy one of the plurality of different machine learning models for the segment;

apply the selected highest accuracy machine learning model for the segment to generate a score each of said members in the segment;

generate a scored member list for electronic display comprising identifying information for each of the members provided in association with the score for each of the members; and automatically initiate medical interventions for at least some of the members in said scored member list based on the member's score, including automatically scheduling a visit by a healthcare provider for at least each member having a score in a first risk category, and automatically scheduling a call by a healthcare provider for at least each member having a score in a second risk category.

2. The system of claim 1 wherein:

said medical data comprises health risk alerts, membership information, consumer information, health program information, CMS data, medical claims, and pharmaceutical claims.

3. The system of claim 1 wherein:

said clinical data comprises claim counts, drug class counts, physician visit counts, and test costs;

said risk data comprises obesity, smoking, prescription risk score, and global risk;

said demographic data comprises race, education level, and active month information; and said features comprise said claim counts, drug class counts, physician visit counts, test costs, obesity, smoking, prescription risk score, global risk, race, education level, and active month information.

4. The system of claim 1 wherein:

the extracted features comprise a demographic profile, clinical profile, behavior profile, medication profile, and disease progression profile.

5. The system of claim 4 wherein:

said demographic profile comprises age, gender, race and socio-economic status;

said clinical profile comprises chronic conditions, mental health conditions, hospitalizations, and medication;

said behavior profile comprises health program participations; and said medication profile comprises adherence to various medications, including diabetes, heart failure, coronary artery disease.

6. The system of claim 1 wherein:

each of said different machine learning models comprise at least one of: a neural network, logistic regression, and decision tree.

7. The system of claim 6 wherein:

at least one of said different machine learning models comprise an ensemble model.

8. The system of claim 1 wherein:

said one or more non-transitory electronic storage devices comprise additional software instructions, which when executed, configure the one or more processors to:

analyze said medical data for standardized codes indicating various diagnosed conditions;

said score is generated, at least in part, by applying a weight to each of said standardized codes associated with any one of: cardiovascular, cerebrovascular, metabolic, nephropathy, neuropathy, peripheral vascular disease, and retinopathy conditions; and categorize each of said members of said population into a high, medium, or low complications risk category based on said score.

9. The system of claim 8 wherein:

said weight comprises a one or a two for each of said conditions, except for neuropathy which is weighted a one;

each of said members having said diabetes complication score ranging from 0-3 are assigned into said low complications risk category;

each of said members having said diabetes complication score ranging from 4-7 are assigned into said medium complications risk category; and each of said members having said diabetes complication score ranging from 8-13 are assigned into said high complications risk category.

10. The system of claim 8 wherein:

said one or more non-transitory electronic storage devices comprise additional software instructions, which when executed, configure the one or more processors to automatically assign a first one of said medical interventions to each of said members categorized into said high complications risk category, assign a second one of said medical interventions to each of said members categorized into said medium complications risk category, and assign a third one of said medical interventions to each of said members categorized into said low complications risk category.

11. The system of claim 10 wherein:

said one or more non-transitory electronic storage devices comprise additional software instructions, which when executed, configure the one or more processors to automatically schedule the visit by the healthcare provider to each of said members categorized into said high complications risk category, and automatically schedule the call by the healthcare provider to each of said members categorized into said medium complications risk category.

12. A system for improving accuracy in predicting the onset, progression, and severity of diabetes complications in a population using population segment specific modeling based on otherwise disparate, siloed sources and automatically initiate member-specific interventions, said system comprising:

databases comprising medical data for a plurality of members of a population, said medical data comprising standardized codes for various diagnoses as part of medical and pharmaceutical insurance claims data and demographic data, said databases including information from a plurality of different, otherwise disparate, siloed data sources, including from a plurality of different providers for at least some of the plurality of members, with different types of available information, at least one publicly accessible source, and at least one privately accessible source;

one or more non-transitory electronic storage devices comprising software instructions, which when executed, configure the one or more processors to:

retrieve said medical data for the members of the population from each of the databases, including from the plurality of otherwise disparate, siloed data sources, and including data from multiple providers for at least some of the members;

perform a pre-processing subroutine on the data received from each of said databases, said pre-processing subroutine comprising multiple stages including summarizing, standardizing, and filtering said data received from each of said plurality of different otherwise disparate, siloed data sources which increases homogeneity of said data;

perform a domain-specific feature extraction subroutine on said pre-processed data which extracts clinically-significant characteristics for said members of the population, said clinically-significant characteristics comprising date of membership to the population, line of business associated with the members, and availability of certain types of said medical data;

segment the population into a plurality of different segments by the characteristics, wherein the characteristics comprise (i) date of membership to the population such that segmentation is performed between new members and existing members, (ii) line of business associated with the member such that segmentation is performed between members associated with different lines of business, and (iii) data availability of certain types of said medical data such that segmentation is performed between members associated with different types of data;

for each of the segments, engage a model selection engine to apply a plurality of different machine learning models to the data for the segment and to test data, said plurality of different machine learning models comprising at least one neural network based model, at least one logistic regression based model, at least one decision tree based model, and at least one ensemble model including a combination of the at least one neural network based model, the at least one logistic regression based model, and the at least one decision tree based model, and each of the plurality of different machine learning models implementing a multi-stage analysis, and select a most accurate one of the plurality of different machine learning models on a segment specific basis, where the most accurate model being determined by model performance against said test data using holdout data, derive a score for each of the members of the segment based on application of the most accurate one of the plurality of different machine learning models to the data for the member;

generate a scored member list comprising identifying information for each of the members provided in association with the score for each of the members;

generate a diabetes complication score for each of said members by applying a weight to each of said standardized codes in the medical data for the respective member associated with any one of: cardiovascular, cerebrovascular, metabolic, nephropathy, neuropathy, peripheral vascular disease, and retinopathy conditions, where the weight applied varies with the condition, and summing the weights;

categorize each of said members within said scored member list into a high, medium, or low complications risk category based on said diabetes complication score;

assign a first intervention to each of said members categorized into said high complications risk category, said first intervention comprising automatically scheduling a provider visit;

assign a second intervention to each of said members categorized into said medium complications risk category, said second intervention comprising automatically scheduling a provider call;

generate a graphical display at one or more remote electronic devices comprising said scored member list, indication of categorization of each of said members, and indication of assignment of said interventions; and automatically initiate said interventions, where assigned.

13. A system for improving accuracy in predicting the onset, progression, and severity of diabetes in a population using population segment specific machine learning modeling based on otherwise disparate, siloed sources, said system comprising:

databases comprising medical data for a plurality of members of a population, wherein said medical data is derived from a plurality of otherwise disparate, siloed data sources, at least one of which is publicly accessible database and at least one of which is privately accessible, said data sources including from a plurality of different providers for at least some of the plurality of members, health risk alerts, membership information, survey information, consumer information, health program information, CMS data, medical claims, pharmaceutical claims, and lab and test result information;

one or more non-transitory electronic storage devices comprising software instructions, which when executed, configure the one or more processors to:

retrieve said medical data for the members of the population from the databases;

pre-process the medical data as part of a multi-stage process including summarizing, standardizing, and filtering to increase homogeneity of the data;

perform a domain-specific feature extraction subroutine on said pre-processed medical data to extract clinically-significant characteristics for said members of the population, the clinically-significant extracted features comprising a demographic profile, clinical profile, behavior profile, medication profile, and disease progression profile, and the characteristics comprising date of membership to the population such that the segmentation is performed between new members and existing members, line of business associated with the member such that the segmentation is performed between members associated with different lines of business, and data availability of certain types of said medical data such that the segmentation is performed between members associated with different types of data;

segment the population into a plurality of segments by at least some of the extracted characteristics;

for each of the segments:

apply each of a plurality of different models to the pre-processed medical data for the respective segment;

apply each of the plurality of different models to a test set of data;

determine which of said plurality of different models provides a highest level of accuracy relative to the test set of data using holdout data; and select and apply the highest accuracy one of the plurality of different models for the respective segment such that a different one of the plurality of different models is applied to the pre-processed medical data for each of the segments, respectively to generate a predicted onset of diabetes score for each of the members;

analyze the pre-processed to extract international classification of diseases (IDC) codes;

analyze the IDC codes to identify if any one or more of: cardiovascular, cerebrovascular, metabolic, nephropathy, neuropathy, peripheral vascular disease, and retinopathy conditions are indicated;

assign a point value to each of identified one of the conditions in the IDC codes, where said point values comprises a one or a two for each of said conditions, except for neuropathy which is weighted a one;

sum the point values to arrive at a diabetes progression score;

categorize the members based on the diabetes progression score, including categorizing each of said members having the diabetes progression score ranging from 0-3 into a low complications risk category, each of said members having the diabetes progression score ranging from 4-7 into a medium complications risk category, and each of said members having diabetes progression score ranging from 8-13 into said high complications risk category;

assign a first intervention to each of said members categorized into said high complications risk category, assign a second intervention to at least each of said members categorized into said medium complications risk category, and assign a third intervention to at least each of said members categorized into said low complications risk category, said first intervention including automatically scheduling a provider visit, and said second intervention including automatically scheduling a provider call;

generate a scored member list for electronic display for the population comprising identifying information for each of the members provided in association with the predicted onset of diabetes score and the diabetes progression score for each of the members;

cause electronic display of said scored member list; and cause the assigned interventions to be carried out for the members.

14. The system of claim 13 wherein:

said one or more non-transitory electronic storage devices comprise additional software instructions, which when executed, configure the one or more processors to:

use a plurality of different ones of the characteristics to segment the population;

use a plurality of different ones of the characteristics to segment a test set of data;

determine which of said plurality of different characteristics provides a highest level of accuracy relative to the test set of data;

select the highest accuracy one of the plurality of different characteristics to segment the population;

said medical data comprises health risk alerts, membership information, survey information, consumer information, health program information, CMS data, medical claims, pharmaceutical claims, and lab and test result information;

said clinical data comprises claim counts, drug class counts, physician visit counts, and test costs;

said risk data comprises obesity, smoking, prescription risk score, and global risk;

said demographic data comprises race, education level, and active month information;

said demographic profile comprises age, gender, race and socio-economic status;

said clinical profile comprises chronic conditions, mental health conditions, hospitalizations, and medication;

said behavior profile comprises health program participations;

said medication profile comprises adherence to various medications, including diabetes, heart failure, coronary artery disease; and the feature comprise said claim counts, drug class counts, physician visit counts, test costs, obesity, smoking, prescription risk score, global risk, race, education level, and active month information.

* * * * *